United States Patent [19]

Cullinan

[11] Patent Number: 4,675,400
[45] Date of Patent: Jun. 23, 1987

[54] BIFUNCTIONAL DERIVATIVES OF 4-DESACETYL INDOLE-DIHYDROINDOLE ALKALOIDS

[75] Inventor: George J. Cullinan, Trafalger, Ind.

[73] Assignee: Eli Lilly and Company, Indianapolis, Ind.

[21] Appl. No.: 745,563

[22] Filed: Jun. 17, 1985

[51] Int. Cl.$^4$ ..................... C07D 519/04; C07K 15/00
[52] U.S. Cl. .................................... 540/478; 530/388;
530/806; 530/809; 530/808; 530/823; 530/825;
530/826; 530/828
[58] Field of Search ................... 260/244.4; 514/283;
540/478

[56] References Cited

U.S. PATENT DOCUMENTS

| | | |
|---|---|---|
| 4,046,722 | 9/1977 | Rowland .................................. 260/6 |
| 4,166,810 | 9/1979 | Cullinan et al. ................... 260/244.4 |
| 4,191,688 | 3/1980 | Conrad et al. ..................... 260/244.4 |
| 4,203,898 | 5/1980 | Cullinan et al. ................... 260/244.4 |
| 4,388,305 | 6/1983 | Trouet et al. ................. 260/244.4 X |
| 4,522,750 | 6/1985 | Ades et al. ....................... 260/112 R |

FOREIGN PATENT DOCUMENTS

| | | |
|---|---|---|
| 124502 | 11/1984 | European Pat. Off. . |
| 2090837 | 1/1982 | United Kingdom . |
| 2111055 | 6/1983 | United Kingdom ............. 260/244.4 |
| 2137210 | 10/1984 | United Kingdom ............. 260/244.4 |
| 2137202 | 10/1984 | United Kingdom . |

OTHER PUBLICATIONS

Blickenstaff et al., Chemical Abstracts, vol. 94, 114277s (1981).
Blickenstaff et al., (I), Cytotoxic Estrogens Horm. Recpt. Tumors, [Proc. Workshop], 1979 (Pub. 1980), pp. 89-105.
FACSS Abstract 183, Root et al., Oct. 6-10, 1975.
Teale et al., Br. J. Clin. Pharm. 4, 169-172 (1977).
Langone et al., Anal. Biochem., 95, 214-221 (1979).
Conrad et al., J. Med. Chem., 22, 391-400 (1979).
Barnett et al., ibid, 21, 88-96 (1978).
Neuss et al., Tetrahedron Letters, No. 7, 783-787, (1968).
Johnson et al., Brit. J. Can., 44, 372, (1981) (pp. 472-475).

Primary Examiner—Nicholas S. Rizzo
Assistant Examiner—Diana G. Rivers
Attorney, Agent, or Firm—Robert A. Conrad; Leroy Whitaker

[57] ABSTRACT

Bifunctional derivatives of a 3-carboxhydrazide of an antineoplastic dimeric indole-dihydroindole alkaloids, useful both in forming conjugates with immunoglobulins and as anti-tumor agents.

13 Claims, No Drawings

BIFUNCTIONAL DERIVATIVES OF 4-DESACETYL INDOLE-DIHYDROINDOLE ALKALOIDS

BACKGROUND OF THE INVENTION

The alkaloids obtainable from *Vinca rosea*, represent one of the most productive areas of chemistry for drugs adversely affecting the growth of experimental malignancies in mammals. Initially, only some of the alkaloids, obtainable from the leaves of the plant by extraction and purifiable by chromatography, were found to be active. These active antineoplastic alkaloids obtained directly from the leaves of the vinca plant included VLB (Vinblastine, vincaleucoblastine), vincristine (leurocristine), leurosine (vinleurosine), leurosidine (vinrosidine), leuroformine (formylleurosine) and deoxy VLB "A" and "B" (4'-deoxy VLB and 4'-deoxyleurosidine). Other less abundant antineoplastic alkaloids have also been formed.

Chemical modification of the Vinca alkaloids started slowly for several reasons. In the first place, the molecular structures involved are extremely complex, and chemists were slow to find reactions which modified one specific functional group of the molecule without affecting other groups. Secondly, dimeric alkaloids lacking desirable chemotherapeutic properties had been recovered or produced from *Vinca rosea* extracts, and a determination of their structures had led to the conclusion that these inactive compounds were closely related structurally to, and even isomeric with, one or more of the active alkaloids. Thus, it appeared that small chemical changes in the known alkaloids could have a profound effect on antineoplastic activity.

Because of these restrictions, modification of the indole-dihydroindole alkaloids obtained from *Vinca rosea* has centered around three areas of the molecule: C—3, C—4' and C—4. Considering C—3 modification first, one of the more recent, and more successful modifications of the basic indole-dihydroindole structure has been the preparation of C—3 carboxamide and carboxhydrazide derivatives, most of which have turned out to be active anti-tumor agents. [See Cullinan et al., U.S. Pat. No. 4,203,898, Conrad et al., U.S. Pat. No. 4,191,688, Cullinan and Gerzon, U.S. Pat. No. 4,166,810. Conrad et al. *J. Med. Chem.*, 22, 391 (1979), and Barnett et al., ibid,; 21 88 (1978)]. One of the amides, 4-desacetyl VLB 3-carboxamide (vindesine), is currently being marketed in several European countries as an oncolytic agent. Vindesine is effective in treating some vincristine-resistant leukemias in addition to many common neoplasms including germ-cell tumors. Secondly, reaction of the 3-hydroxy and 3-ester functions of a indole-dihydroindole *vinca* alkaloid with an isocyanate has produced the corresponnding oxazolidinedione derivatives, one of which, the N-chloroethyl derivative—vinzolidine—is currently undergoing a clinical trial in humans. These oxazolidinedione derivatives are disclosed in Miller and Gutowski, U.S. Pat. No. RE 30,560, reissued Mar. 31, 1981. Trouet et al., U.S. Pat. No. 4,388,305 (same as EPO 41,935) discloses anti-cancer VLB C—3 peptides in which the peptide group contains 1-6 amino acid residues with a terminal free acid or ester group. Amides of this class derived from a single amino acid are also disclosed in Cullinan et al. U.S. Pat. No. 4,203,898 (col. 15, lines 1-16). The hydrazide-azide synthetic procedure of Cullinan et al., is also employed by Trouet et al. to prepare their amides.

A second area of the molecule which has been modified with retention of anti-tumor activity is the C—4' functionality. A majority of these modifications have been based on the 3', 4'-anhydro derivative, makeable both by coupling vindoline and catharanthine via a modified Polonovski reaction—Potier et al. *J.C.S. Chem. Comm.*, 670, (1975)—and by dehydrating VLB or leurosidine—Gutowski and Miller, U.S. Pat. No. 4,029,663. The dehydration reaction produces two exodouble bond isomers in addition to the $\Delta^{3',4'}$-anhydro derivative. Functionalization of any one of these double bonds to form epoxides, diols, etc. has constituted the chief chemical modifications undertaken at C—4'.

The third region of the indole-dihydroindole which has been modified successfully is C—4. In the first place, hydrolysis of the acetoxy group, present in all the naturally-occurring vinca alkaloids, yields active antineoplastic 4-desacetyl derivatives. (Vindesine, a C—3 carboxamide, is a 4-desacetyl derivative.) Secondly, Hargrove, U.S. Pat. Nos. 3,387,001 and 3,392,173 prepared novel 4-acyl derivatives of 4-desacetyl VLB, 4-desacetyl vincristine, etc. Among these new derivatives was 4-chloroacetyl VLB, an antineoplastic compound which compound could be further reacted with amines; for example, dimethylamine, to yield a potent anticancer drug, vinglycinate, N,N-dimethyl 4-glycinyl VLB. In a different modification, Wright and Neuss, U.S. Pat. No. 4,122,082, oxidized the 4-hydroxyl of 4-desacetyl VLB to a 4-keto compound, and Thompson, U.S. Pat. No. 4,195,022, reduced this ketone to the 4-epihydroxy (4α-hydroxy) derivative, also a compound with anti-cancer activity.

In addition to the VLB/VCR etc. hydrazide from Cullinan et al, (loc. cit.) and leurosine hydrazide disclosed in Neuss, Gorman, Cone and Huckstep, *Tetrahedron Letters* 783 (1968) (This article, in Table I, page 785, refers to compound XI as VLB hydrazide, but according to the footnote, the compound is actually an 18'-descarbomethoxy derivative-see also line 2 for the correct name for XI). Derivatives of 4-desacetyl VLB hydrazide are disclosed in Cullinan and Gerzon, U.S. Pat. No. 4,166,810. The named derivatives include mono $C_{1-3}$ alkyl, β-hydroxyethyl, β-acetoxyethyl $C_{2-4}$ alkanoyl, dichloroacetyl, benzoyl $C_{1-3}$ alkylcarbazyl, dimethyl and $C_{1-3}$ alkylidine (=CRR' where R and $R^1$ are H or methyl or one is ethyl).

Indole-dihydroindole bridged tetramers; i.e., the same or different dimeric alkaloid moieties bridged thru the 3-carboxyl via a bis-amide are described in Conrad and Gerzon, U.S. Pat. No. 4,199.504. Otherwise, indole-dihydroindole vinca alkaloid dimers have not been prepared by bridging through other positions to form vinca tetramers.

VLB and vincristine have been conjugated with proteins to form antigens useful in radioimmune assays 4-Desacetyl VLB 3-carboxazide (4-desacetyl vinblastinoic azide) and the corresponding vincristine compound were the derivatives employed; see Conrad et al., *J. Med., Chem.*, 22, 391 (1979), Root et al, Abstract 182, FACSS, Oct. 6, 1975, and U.S. Pat. No. 4,203,898 Langone et al, *Anal. Biochem.*, 95, 214 (1979) and Teale et al, *Brit. J. Clin. Pharm.*, 4, 169 (1977) for illustrations of this reaction. In some of these instances, the coupling agents were the C—3 carboxazides. In another reference, the alkaloid and protein were coupled via a Mannich reaction involving an unspecified portion of the vinca molecule. The C—3 carboxylic acid has also been used to couple directly to amino groups of a protein via a carbodiimide intermediate.

In testing these conjugates, Johnson et al, *Brit. J. Can.*, 44, 372 (1981) disclose the cytotoxic action vs. human cancer cells of a vindesine-anti-CEA immunoglobulin conjugate prepared from 4-desacetyl VLB azide. This same information is disclosed in Rowland and Simmonds, Ser. No. 332,023 filed Dec. 18, 1981, now abandoned in a continuation-in-part thereof, Ser. No. 528,715, filed Sept. 2, 1983 now abandoned, and in a continuation application thereof, Ser. No. 755,221, filed July 15, 1985. Finally, Rowland, U.S. Pat. No. 4,046,722, claims immunoglobulins with a covalently-bound cytotoxic drug attached thereto.

DESCRIPTION OF THE INVENTION

This invention provides compounds of the formula

V—NH—NH—CO—X—COZ    I wherein V is a dimeric indole-dihydroindole radical of formula II derived from an antineoplastic dimeric indole-dihydroindole alkaloid,

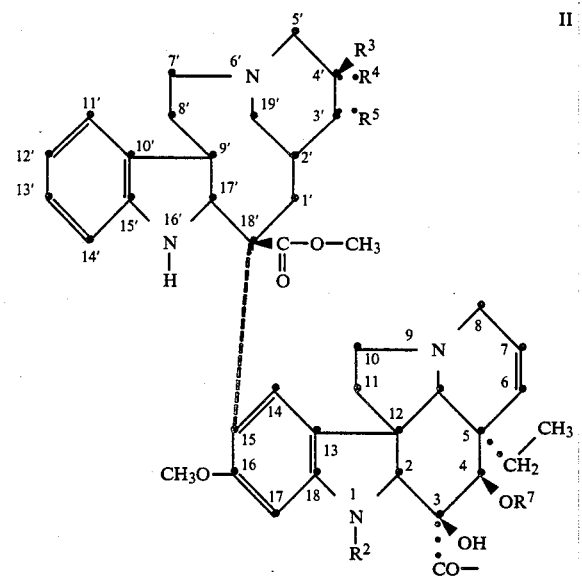

wherein $R^2$ is H, $CH_3$ or CHO; when $R^4$ and $R^5$ are taken singly, $R^5$ is H, and one of $R^3$ and $R^4$ is ethyl and the other is H or OH; when $R^4$ and $R^5$ are taken together with the carbons to which they are attached, they form an oxirane ring in which case $R^3$ is ethyl; and $R^7$ is H, chloro $C_{1-3}$ alkyl—CO or $C_{1-3}$ alkyl—CO, wherein Z is OH, O—$C_1$—$C_3$ alkyl, $NH_2$, NH—$NH_2$, $Z^1$, an acylating group including but not limited to

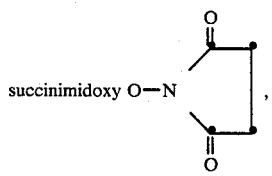

succinimidoxy O—N

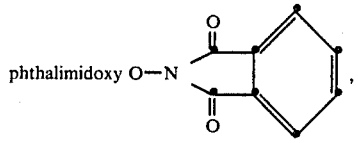

phthalimidoxy O—N

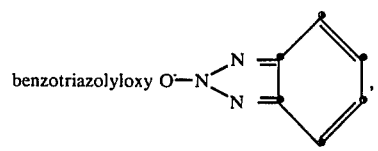

benzotriazolyloxy O—N or O-CO-$C_{4-7}$alkyl, or $Z^2$, a carboxy protecting group such as $CCl_3CH_2O$, $CBr_3CH_2O$, $CH_2ICH_2O$, benzyloxy, methylbenzyloxy, t-butyloxy, allyloxy, methoxybenzyloxy, nitrobenzyloxy, phenacyloxy, nitrophenacyloxy, methoxyphenacyloxy, methylphenacyloxy, diphenylmethyloxy, trityloxy(triphenylmethyloxy), trimethylsilyloxy or the like carboxy-protecting groups; and wherein X is $C_{1-4}$ straight-chain alkylene, $C_{2-8}$ branched chain alkylene, $C_{2-4}$ alkenylene, $C_{3-4}$ alkynylene, $C_{3-6}$ cycloalkylene, phenylene, or a direct bond; and acid addition salts thereof.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxyalkanoic and hydroxyalkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, naphthalene-1-sulfonate, naphthalene-2-sulfonate, mesylate and the like salts.

The compounds of this invention in which Z is $NH_2$, NH—$NH_2$, OH or O—$C_{1-3}$ alkyl have utility as anti-tumor compounds in transplanted tumors in mice, and also possess antimitotic properties.

When Z is a carboxy activating (acylating) group ($Z^1$), it can be any of the relatively well-known acylating groups employed in the chemical art and in particular those used in peptide chemistry as carboxy activating groups. Such groups are discussed, generally, for example, in *Peptide Synthesis*, M. Bodanszky, Y. S. Klausner and M. A. Ondetti, Second Edition (John Wiley & Sons, New York, New York, 1976) notably pages 85 to 136. However, because of the fact that cyclic hydrazinimido derivatives of the structure

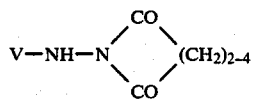

can be formed when an attempt is made to convert an intermediate of the formula V—NH—NH—CO—$(CH_2)_{2-4}$—COOH to a moiety capable of acylating an immunoglobulin; ie, V—NH—NH—CO—$(CH_2)_{2-4}$—$COZ^1$ where $Z^1$ is a small acylating moiety such as Cl, Br, $N_3$, $OCOCH_3$ and the like. For a more complete exposition of the chemistry of the above cyclization process, in which a $Z^1$ type of group can cause cyclization to occur, see my copending application Ser. No. 745,562, filed June 17, 1985. At any rate, the $Z^1$ moieties as defined above all have sufficient bulk to inhibit the afore-mentioned cyclization reaction, while at the same time providing sufficient acylating potential to enable one skilled in the art to prepare immune conjugates having the structure

where Ig is an immunoglobulin, preferably also a monoclonal antibody.

As set forth above, not all small activating groups cause cyclization and care must be taken in choosing the activity group depending on whether one desires to prepare a cyclic imide or an immunogloublin conjugate. However, regardless of the size of the acylating group, if the intermediate V—NH—NH—CO—$(CH_2)_{2-4}$-$COZ^1$ is reacted immediately with the immunogloublin (before it has time to cyclize on itself), reasonable yields of the conjugates V-CO-NH-NH-$(CH_2)_{2-4}$—COIg can be prepared.

When Z is a carboxy protecting group ($Z^2$), any of the other well-known groups employed for this purpose, in addition to those set forth above, are encompassed within that term. Thus, the term "carboxy protecting group" as used herein refers to the commonly used carboxylic acid protecting groups employed to block or protect the carboxylic acid functionality while reactions involving other functional sites of a compound are being carried out. Such carboxy protecting groups are noted for their ease of cleavage by hydrolytic or by hydrogenolytic methods to yield again the original carboxylic acid.

Groups illustrative of X in the above formulas include methylene, ethylene, propylene, butylene, vinyl, propenylene, butenylene, butynylene, ethynylene, 1,2-dimethylethylene, 3,4-dimethylbutylene, 1,4-cyclohexylene, 1,4-phenylene, 1,2-phenylene and the like.

The synthesis of the compounds of this invention is carried out in stepwise fashion. First, a vincahydrazide of the formula V—NH—$NH_2$, wherein $R^7$ in V is OH and the other terms in V have their usual significance, is prepared by reacting a compound of the formula V—$OCH_3$ (wherein $R^2$—$R^5$ and $R^7$ have their previous meanings) with hydrazine according to Conrad et al-loc.cit. The product of this reaction is a compound of the formula V—NH—$NH_2$ wherein, in part structure V, $R^2$—$R^5$ have their previous meaning but $R^7$ is H, the acetoxy group at C—4 being hydrolysed under the reaction conditions. These vinca carboxyhydrazides are then used in succeeding acylation reactions as follows.

First, any of the above 4-desacetyl vinca hydrazides (V—NH—$NH_2$) can be acylated with an anhydride of the formula

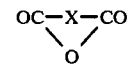

or with a half acid chloride ester ($C_{1-3}$ alk-O-CO-X-CO-Cl or the like) to yield a compound of the formula V-NH-NH-CO-X-O-Z wherein Z is OH, or O-$C_{1-3}$ alkyl. Compounds wherein Z is O-$C_{1-3}$ alkyl can also be prepared from the half-acid, V-NH-NH-CO-X-COOH, via one of the usual esterification procedures using a $C_{1-3}$ alkanol. Methanol is the preferred alkanol since the other ester groups present in starting materials of the formula V-NH-$NH_2$ are methyl esters and transesterification problems are largely avoided by the use of a methanolic environment.

Other acylating groups can be used in place of Cl to prepare the half acid ester V-NH-NH-CO-X-$COOC_{1-3}$ alkyl. The acylating moiety can thus be represented generally by the formula

wherein X has its previous meaning and $Z^1$ is Cl, Br, $N_3$ succinimidoxy, phthalimidoxy, methanesulfonyloxy, toxyloxy, phenylsulfonyloxy, benzotriazolyloxy, or other acylating moiety. Alternatively, an acylating agent of the formula $Z^1$-CO-X-CO-$Z^2$ where $Z^2$ is a carboxy protecting group, can be used to yield a compound of the formula VCO-X-CO-$Z^2$ and eventually after removal of the protecting group, VY-CO-X-COOH where Y is -NH-NH, and X has its previous meaning.

If it is desired to prepare derivatives wherein the C-4 hydroxyl is acylated; i.e., $R^7$ in V is acetyl or another acyl group, one can use, for example, the procedures of Hargrove, U.S. Pat. No. 3,392,173, or of Cullinan, U.S. Pat. No. 4,012,390. These acylations can be carried out on a compound of the structure V-NH-NH-CO-X-COZ where Z is either $OC_{1-3}$ alkyl or $Z^2$, a carboxy protecting group, where $R^7$ in V is OH and where X has its previous significance. It should be pointed out, though it may be obvious to those skilled in the art, that bifunctional hydrazide derivatives where Z is OH; ie, a free carboxylic acid, are not acylable at C—4 without concomitant cyclization on the hydrazide group.

If, as it frequently does, acylation at C—4 also produces some acylation of the C—3 hydroxyl, the time-honored procedure of Hargrove -loc.cit.- is available; ie., the use of wet silica gel to hydrolyze selectively the C—3 acyl group.

Compounds according to I in which Z is $NH_2$ or $NHNH_2$ are prepared by forming an "activated" vinca dimer (V group) 3-hemi-acid derivative of the formula

where $Z^1$ is a noncyclizing bulky carboxy activating group as defined above. Conveniently, a mixed anhydride is formed from the half-acid (Z=OH) by treatment successively with N-methylmorpholine and an alkyl chloroformate. Reaction of the mixed anhydride with alcoholic ammonia or hydrazine yields the desired half-amide.

Alternative procedures for preparing several of the compounds of formula I involve the use of coupling agents such as DDC—dicyclohexylcarbodiimide—, EEDQ-N-ethoxycarbonyl-2-ethoxy-1,2-dihydroquinoline—etc. under anhydrous reaction conditions with a half-acid, $HO\text{-}CO\text{-}X\text{-}CO\text{-}Z^2$, wherein $Z^2$ is a carboxy-protecting group. For example, an initial 4-succinoxy derivative can be prepared from $V\text{-}NH\text{-}NH_2$ and $HO\text{-}CO\text{-}X\text{-}CO\text{-}Z^2$ in the presence of DCC to yield a compound of the formula

V-NH-NH-CO-X-CO-Z².

The carboxy protecting group can then be removed and the resulting free acid reacted with hydroxythalimide, hydroxybenzotriazole, hydroxysuccinimide or the like to yield reactive acylating intermediates of the formula

V-NH-NH-CO-X-CO-Z¹.

wherein $Z^1$ is succinimidoxy, benzotriazolyloxy or phthalimidooxy and X has its previous significance.

All such intermediates containing an acylating moiety, $Z^1$, react with protein to form conjugates useful, for example, in a radioimmune assay or, where the protein is a polyclonal or monoclonal antibody, in treating cancer. As previously stated, where a non-bulky acylating group Z' is used, the reaction between the immunoglobulin and the VCONHNHCOXCOZ' acylating derivative should take place in situ shortly after the acylating derivative has been formed to avoid the self-cyclization reaction. In addition, the "activated" ($Z^1$) derivatives can be reacted with a lower alcohol to yield half esters of the formula V-NH-NH-CO-X-COOC₁₋₃ alkyl provided, if $Z^1$ is non-bulky, the reaction takes place as soon as the $Z^1$ group is in place, as by quenching the reaction mixture with the desired lower alcohol.

Thus, generally speaking, the compounds of this invention of the structure $V\text{-}NH\text{-}NH\text{-}CO\text{-}X\text{-}CO\text{-}Z^1$ are useful intermediates.

Starting indole-dihydroindole alkaloids useful in forming the compounds of this invention, can be represented by the following 2-dimensional structure

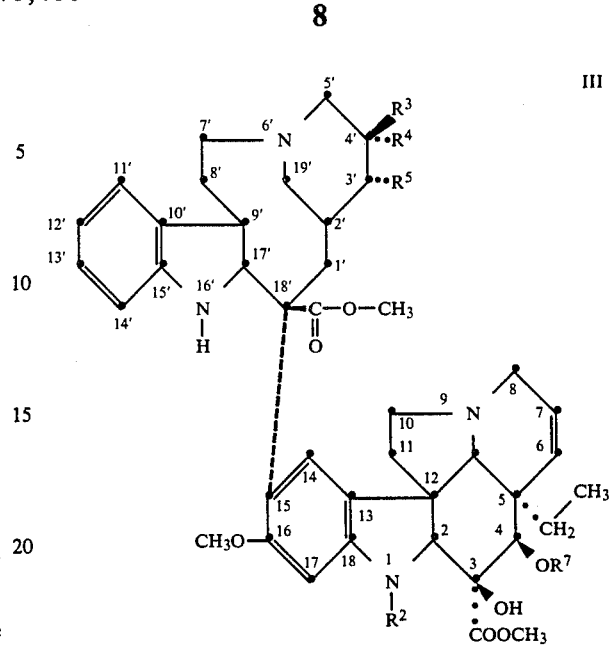

wherein $R^2$ is H, $CH_3$ or CHO; when $R^4$ and $R^5$ are taken singly, $R^5$ is H and one of $R^3$ and $R^4$ is ethyl and the other is H or OH; when $R^4$ and $R^5$ are taken together with the carbons to which they are attached, they form an oxirane ring, in which case $R^3$ is ethyl; and $R^7$ is acetyl. Compounds represented by III above are initially reacted with hydrazine to yield 4-desacetyl carboxhydrozides of the structure $V\text{-}NH\text{-}NH_2$ wherein $R^7$ is OH.

In formula III above, where $R^7$ is $CO\text{-}CH_3$, $R^2$ is methyl, $R^3$ is hydroxyl, $R^4$ is ethyl and $R^5$ is H, VLB (vinblastine) is represented; where $R^7$ is $CO\text{-}CH_3$, $R^2$ is formyl, $R^3$ is hydroxyl, $R^4$ is ethyl and $R^5$ is H, vincristine (VCR) is represented; where $R^7$ is $CO\text{-}CH_3$, $R^2$ is methyl, $R^3$ is ethyl, $R^4$ is hydroxyl, and $R^5$ is H, leurosidine is represented; where $R^7$ is $CO\text{-}CH_3$, $R^2$ is methyl or formyl, $R^3$ is ethyl and $R^4$ and $R^5$ taken together with the carbons to which they are attached form an alpha-epoxide ring, leurosine and leuroformine, respectively, are represented; where $R^7$ is $CO\text{-}CH_3$, $R^2$ is methyl, $R^3$ is ethyl, $R^4$ and $R^5$ are H, deoxy VLB "B" or 4'-deoxyleurosidine or 4'-epideoxy VLB is represented; where $R^7$ is $CO\text{-}CH_3$, $R^2$ is methyl, $R^4$ is ethyl and $R^3$ and $R^5$ are H, deoxy VLB "A" or 4'-deoxy VLB is represented; and where $R^7$ is $CO\text{-}CH_3$, $R^2$ is CHO, $R^3$ is ethyl, $R^4$ and $R^5$ are H, 4'-epideoxyvincristine (1-formyl-1-desmethyl-4'-deoxyleurosidine) is represented. Replacement of the C—3 carbomethoxy with carboxamide and hydrolysis of the C—4 acetoxy gives vindesine (VDS).

Literature references to the parent vinca alkaloids (III, are as follows: leurosine (U.S. Pat. No. 3,370,057), VLB (U.S. Pat. No. 3,097,137), leurosidine (vinrosidine) and leurocristine (to be referred to hereafter as vincristine) (both U.S. Pat. No. 3,205,220), desmethyl VLB (U.S. Pat. No. 3,354,163), 4'-epivincristine (U.S. Pat. No 4,143,041) leuroformine, formylleurosine (U.S. Pat. No. 4,279,816), and deoxy VLB "A" and "B" [*Tetrahedron Letters*, 783 (1958)].

The preparation of typical compounds according to formula I is illustrated below.

EXAMPLE 1

Preparation of $N^2$-Succinoyl-4-desacetyl VLB 3-carboxhydrazide

A solution was prepared from 4.57 g of 4-desacetyl VLB 3-carboxhydrazide [(prepared by the procedure of Conrad et al., *J. Med. Chem.* 22, 391, (1979)] in 25 ml of pyridine. 655 mg of succinic anhydride were added. Reaction mixture was sealed under a nitrogen atmosphere at room temperature and protected from the light. The sealed reaction mixture was allowed to stand for 3 days at ambient temperature, and was then opened, tlc on an aliquot partitioned between water and methylene dichloride indicated an absence of starting material. The reaction mixture was therefore evaporated to dryness, and the resulting residue dissolved in anhydrous ethanol. The reaction mixture was again evaporated to dryness, and this residue recrystallized from anhydrous ethanol. 2.36 g of crystalline $N^2$-succinoyl-4-desacetyl VLB-3-carboxhydrazide were obtained plus an additional 970 mg of product from the mother liquor.

The compound had the following physical characteristics: TLC; $R_f$=0.09. (silica gel 1:1 ethyl acetate/methanol).

Infrared spectrum (chloroform): peaks at 3455, 3400, 1719, 1675, 1615 cm$^{-1}$.

pKa (66% DMF)=5.1, 6.6 and 7.8 (approximate molecular weight=853.)

NMR (CDCl$_3$)DSMO$_{d6}$ δ at 0.93, 2.85, 3.62, 3.77, 4.05, 5.70, 5.82, 5.92, 6.47, 7.16, 7.52, 9.16, 9.75.

EXAMPLE 2

Preparation of mixed anhydride of $N^2$-Succinoyl 4-desacetyl VLB 3-carboxhydrazide and Isobutylorthoformic acid A solution is prepared from 1 g of $N^2$-succinoyl 4-desacetyl VLB 3-carboxhydrazide, 100 ml of methylene dichloride and sufficient THF to give a homogenous reaction mixture. 350 mg of N-methyl morpholine were added. The reaction mixture was cooled in an ice bath to about 0° C. 400 mg of isobutyl orthochloroformate were added and the reaction mixture was sealed under a nitrogen atmosphere and stirred. After about 45 minutes, the reaction vessel was opened and the volatile constituents removed in vacuo. The resulting residue, comprising the mixed anhydride of N—$^2$ succinoyl 4-desacetyl VLB 3-carboxhydrazide and isobutylorthoformate was triturated with ether and the ether decanted. Residual ether was removed in vacuo. The mixed anhydride thus prepared had the following physical characteristics:

Infrared spectrum (chloroform): peaks at 3470, 3360, 1835, 1736, 1685, 1612 cm$^{-1}$.

NMR (CDCl$_3$): δ at 0.95, 2.84, 3.62, 3.80, 5.78, 5.85, 6.10, 7.20, 7.46, 10.19.

EXAMPLE 3

Preparation of $N^2$-Succinoyl 4-desacetyl VLB 3-carboxhydrazide N-hydroxy succinimide ester Following the procedure of Example 2, 500 mg of the mixed anhydride of $N^2$-succinoyl-4-desacetyl VLB 3-carboxhydrazide and isobutyl orthoformate were dissolved in 25 ml of methylene dichloride. 175 mg of N-methylmorpholine were added, and the reaction mixture sealed under nitrogen. The reaction mixture was placed in an ice bath. 195 mg of isobutyl orthochloroformate were added and this new mixture stirred at ice bath temperature for about 45 minutes. The volatile constituents were then removed in vacuo, and the resulting residue triturated twice with ether and then dried. The residue was dissolved in 25 ml of methylene dichloride and 400 ml N-hydroxysuccinimide were added to the solution. This new reaction mixture was again sealed under a nitrogen atmosphere and placed in a hot water bath where it was stirred for about 45 minutes. The volatile constituents were then removed in vacuo, and the residue triturated twice with ether and then dried. The residue was then dissolved in methylene dichloride and the methylene dichloride solution washed with water and then dried. Evaporation of the volatile constituents from the dried solution yielded 220 mg of $N^2$-Succinoyl 4-desacetyl VLB 3-carboxhydrazide N-hydroxysuccinimide ester. The compound had the following nmr spectrum: δ at 0.96, 2.52, 2.84, 3.62, 3.80, 4.06, 5.74, 5.86, 6.09, 6.52, 7.17, 7.48, 8.07.

EXAMPLE 4

Preparation of $N^2$-Succinoyl 4-desacetyl VLB 3-carboxhydrazide methyl ester

Following the procedure of Example 2, 1 gm of $N^2$-succinoyl 4-desacetyl VLB 3-carboxhydrazide in 25 ml of methylene dichloride was reacted with 400 mg of N-methylmorpholine in the presence of 10 ml of pyridine. The reaction mixture was cooled and 300 mg of isobutyl orthochloroformate added. This reaction mixture was stirred for about 5 minutes at about 0° at which time 20 ml of methanol were added. The reaction mixture was allowed to remain at room temperature overnight. 170 mg of $N^2$-succinoyl 4-desacetyl VLB 3-carboxhydrazide methyl ester were obtained by removal of the solvent and chromatography (HPLC) of the residue over silica with a gradient of ethyl acetate to ethylacetate/methanol 1:1. The compound had the following physical characteristics:

TLC; $R_f$=0.45 (silica gel, ethyl acetate/methanol 1:1)

infrared spectrum (chloroform): 3480, 3410, 1733, 1675, 1640, 1615 cm$^{-1}$.

NMR (CDCl$_3$): δ at 0.92, 0.95, 2.82, 3.62, 3.72, 3.79, 4.14, 5.82, 6.09, 6.60, 7.14, 7.54, 8.48, 9.15, 9.82.

EXAMPLE 5

Preparation of $N^2$-Succinoyl 4-desacetyl VLB 3-carboxhydrazide amide 100 mg of the mixed anhydride of Example 2 were dissolved in 10 ml of THF to which solution was added 1 ml of 1N aqueous ammonium hydroxide. After several hours at room temperature, the reaction mixture was evaporated to dryness, and the residue dissolved in chloroform. The chloroform solution was washed with water and then dried. Evaporation of the chloroform yielded 30 mg of $N^2$-Succinoyl 4-desacetyl VLB 3-carboxhydrazide amide having the following physical characteristics:

TLC; $R_f$=0.25 (silica gel, ethyl acetate/methanol 1:1)

infrared spectrum (chloroform): 3470, 3400, 1718, 1674, 1615 cm$^{-1}$

NMR (CDCl$_3$) δ at 0.93, 2.81, 3.60, 3.78, 4.10, 5.78, 6.12, 6.60, 7.16, 7.54, 8.10, 9.83.

EXAMPLE 6

Preparation of $N^2$-Succinoyl 4-Desacetyl-4'-deoxyleurosidine 3-carboxhydrazide.

A solution was prepared by dissolving 1320 mg of 4-desacetyl-4'-deoxyleurosidine 3-carboxhydrazide in 25 ml of pyridine. 175 mg of succinic anhydride were added and the reaction mixture stirred at room temperature under a nitrogen blanket for about 24 hours. TLC on silica showed a new major spot; $R_f=0.065$. The reaction mixture was therefore evaporated to dryness and the residue dissolved in a mixture of methylene dichloride and methanol. The organic layer was washed twice with equal volumes of water and then dried. Evaporation of the solvent yielded $N^2$-succinoyl-4-desacetyl-4'-deoxyleurosidine 3-carboxhydrazide.

EXAMPLE 7

Preparation of $N^2$-Adipoyl-4-desacetyl VLB C-3-carboxhydrazide methylester

A solution was prepared by dissolveing 250 mg of 4-desacetyl VLB 3-carboxhydrazide in 50 ml of methylene dichloride. One ml of pyridine was added followed by 58 mg of adipoyl half acid chloride methylester. The reaction mixture was sealed under nitrogen at room temperature for 24 hours. The sealed reaction vessel was opened, and the solvent removed by evaporation in vacuo. The residue was dissolved in a mixture of methylene dichloride plus a minimal amount of ethanol. The organic layer was washed with water and then dried. Evaporation of the following yielded a residue comprising $N^2$-adipoyl-4-desacetyl VLB 3-carboxhydrazide methylester formed in the above reaction having the following physical characteristics.

Mass spectrum: molecular ion at 910, consistent with $C_{50}H_{66}N_6O_{10}$.

Infrared spectrum (chloroform): peaks at 3020–2953, 1730, 1680, 1616 cm$^{-1}$.

NMR: $\delta$ at 8.17, 7.53, 7.18, 6.55, 6.08, 5.85, 5.74, 4.09, 3.78, 3.68, 3.60, 3.58, 2.82, 2.33, 1.67, 0.92.

A sulfate salt was prepared from 2% ethanolic sulfuric acid (prepared by dissolving 1 gm of 18 molar sulfuric acid in 49 g of anhydrous ethanol). The pH of the solution was lowered to about 2.0 and the solution was then back titrated with 0.1N aqueous sodium hydroxide. The reaction mixture was filtered and the solvent evaporated to dryness in vacuo leaving 72 mg of the sulfate salt of $N^2$-adipoyl-4-desacetyl VLB 3-carboxhydrazide methylester as a residue.

EXAMPLE 8

Preparation of $N^2$-Glutaroyl 4-desacetyl VLB 3-carboxhydrazide

A solution was prepared by dissolving 500 mg of 4-desacetyl VLB 3-carboxhydrazide in 50 ml of methylene dichloride. Two ml of pyridine was added followed by 75 mg of glutaric anhydride. The reaction mixture was sealed under a nitrogen atmosphere and kept at room temperature for about 24 hours. The sealed reaction vessel was then opened and crystals, which had precipitated, were separated by filtration; yield=about 50 mg. The filtrate was evaporated to dryness in vacuo. The resulting residue was dissolved in anhydrous ethanol and the pH adjusted to about 4.0 with 2% ethanolic sulfuric acid. The acidic mixture was kept at about 0° C. for 48 hours and was then filtered. The filter cake was washed with ether. Fifty-eight mg of $N^2$-glutaroyl 4-desacetyl VLB 3-carboxhydrazide sulfate were obtained.

A small amount of the sulfate salt was converted to the corresponding free base by standard procedure. The free base had the following physical characteristics.

$pK_a$ at 4.8, 6.5, 7.7 (66% DMF).

NMR: $\delta$ at 10.0, 8.16, 7.48, 7.09, 6.54, 6.07, 5.81, 5.70, 3.77, 3.59, 2.84, 0.92.

EXAMPLE 9

Preparation of salts

About 120 mg of $N^2$-succinoyl-4-desacetyl VLB 3-carboxhydrazide methyl ester from Example 6 were dissolved in anhydrous ethanol and the pH thereof adjusted to about 3.0 with freshly prepared ethanolic sulfuric acid (1.4 g of 18M aqueous sulfuric acid in 48.6 g of ethanol). The reaction mixture was evaporated to dryness in vacuo. 40 mg of a white, amorphous powder were obtained, comprising the sulfate salt of $N^2$-succinoyl 4-desacetyl VLB 3-carboxhydrazide methyl ester.

Other salts are prepared in analogous fashion.

The following illustrates the scope of the compounds represented by II above. In naming these compounds, where a group present in the original indoledihydroindole dimer has been replaced by a new function; i.e., (3-carbomethoxy) replaced by 3-carboxhydrazide, the group removed will be omitted.

$N^2$-succinoyl 4-desacetyl-4'-deoxy VLB 3-carboxhydrazide maleate, $N^2$-glutaroyl-4'-deoxyleurosidine 3-carboxyhydrazide ethyl ester hydrochloride, $N^2$-adipoyl 4-chloroacetyl-4'-deoxy 1-formylleurosidine 3-carboxhydrazide amide, $N^2$-terephthaloyl 4-desacetylleurosidine 3-carboxhydrazide N-hydroxysuccinimide ester, $N^2$-phthaloyl vincristine 3-carboxhydrazide ethyl ester and the like.

The compounds of this invention in which Z is OH, $NH_2$, $NHNH_2$, or $O-C_{1-3}$ alkyl have utility as antitumor compounds acti transplanted tumors in mice, as mitotic inhibitors and as cytotoxic agents. As evidence of such utility, the ability of $N^2$-succinoyl 4-desacetyl VLB 3-carboxhydrazide methyl ester sulfate to cause metaphase arrest was measured by standard procedures. This compound blocked growing tumor cells in mitosis at a concentration of 0.2 mcg/ml.

The compounds of the present invention also inhibit the growth of human leukemic cells (CCRF-CEM cell line). Table 1 below gives the results of testing of several compounds representated by Formula II above. In the Table, column 1 gives the name of the compound and column 2, the $IC_{50}$ (concentration giving 50% growth inhibition) in mcg/ml.

TABLE 1

| C.C.R.F.-C.E.M. Cytotoxicity Assay | |
|---|---|
| Compound Name | $IC_{50}$ mcg/ml |
| $N^2$—Adipolyl 4-desacetyl VLB 3-carboxhydrazide methyl ester sulfate | 0.4 |
| $N^2$—Glutaroyl 4-desacetyl VLB 3-carboxhydrazide sulfate | 0.1 |

Certain of the above compounds have also shown activity against a transplanted tumor, 6C3HED lymphosarcoma, in mice. Information as to this activity is summarized in Table 2 in which column 1 gives the name of the compound, column 2, the dose level in mg./kg. and column 3 the percent tumor inhabitation. All compounds were administered on day one by the intravenous route.

TABLE 2

| Name of Compound | Dose mg/kg | % Tumor Inhibition |
|---|---|---|
| $N^2$—Succinoyl 4-desacetyl VLB 3-carboxhydrazide, methyl ester sulfate | 4 | Toxic |
| | 2 | Toxic |
| | 1 | 100 |
| | .5 | 100 |
| $N^2$—Succinoyl 4-desacetyl VLB 3-carboxhydrazide sulfate | 40 | 100 |
| | 20 | 100 |
| | 10 | 77 |
| | 5 | 33 |
| | 2.5 | 5 |
| | 1.25 | 5 |
| | 0.625 | 13 |

This invention also provides novel conjugates comprising a vinca alkaloid moiety covalently linked at the 3-carboxyl of the vinca alkaloid via a group of the formula NH—NH—COXCO— to an immunoglobulin or an immunoglobulin fragment. In the part formula, X represents a single chemical bond or an aliphatic or cycloaliphatic chain, or a phenylene group. The vinca is conjugated to the protein via an acylating moiety $Z^1$ attached to the terminal carbonyl. The novel conjugate thus prepared is formed with a 3-carboxyhydrazide derivative of a neoplastic dimeric indole-dihydroindole alkaloid, (VLB, deoxy VLB "B" etc.). The conjugates can have one or more such vinca alkaloid moieties attached by a dicarboxyl derivative to the immunoglobulin. The conjugated immunoglobulin, particularly a conjugated monoclonal antibody, attaches itself to the cell wall of a tumor cell, the antineoplastic vinca alkaloid may be released to give a high concentration locally of the alkaloid in the neighborhood of the cell or the conjugate may have antineoplastic activity in the undissociated state.

The immunoglobulin or immunoglobulin fragment, a part of these conjugates, is an antibody, preferably a monoclonal antibody, or a fragment of an antibody, with antigen recognising properties. The preferred immunoglobulin material is an antibody, or a fragment of an antibody adapted for recogition of antigens on the surface of unwanted cells, particularly tumor cells of the type occurring in the human body. However immunoglobulin materials of other kinds are also included within the scope of the invention since they may be of use in treatment of animals and in control and assay experiments.

This invention also includes conjugates for use in an indirect system in which they are employed to recognise an antibody specific to the cell surface antigen.

More particularly, the preferred conjugates of this invention, those attached to the vinca thru a hydrazide group can be represented by the following formula

in which Ig represents an immunoglobulin. Immunoglobulin fragments (Ig') also form useful conjugates. V and X are as defined above. The immunoglobulin, or fragment thereof, can be modified by one or more of the coupled vinca residues shown, preferably up to ten of such coupled vinca residues per immunoglobulin.

Immunoglobulins specific to antigens on the surface of cells to be killed, and techniques for their production from the serum of immunized animals or by culturing hybridomas secreting monoclonal products, are well known. The preferred type of antibody for use in the invention is an immunoglobulin of the IgG or IgM classes. Some representative immunoglobulins are as follows, mono- or polyclonal antibodies to.
  (i) human or animal tumour associated antigens
  (ii) human B- and T-cell antigens
  (iii) human Ia antigens
  (iv) viral, fungal and bacterial antigens
  (v) cells involved in human inflammatory or allergic reactions Of the preferred antibodies to human or animal tumour associated antigens there may be mentioned:
  (i) Ig from goats or sheep immunised with carcinoembryonic antigen
  (ii) Ig from rabbit antiacute lymphoblastic leukemia serum
  (iii) Ig from various primate antisera raised against acute lymphoblastic leukemia, acute myeloblastic leukemia, chronic lymphoblastic leukemia and chronic granulocytic leukemia
  (iv) Ig from goats or sheep immunised with lung carcinoma material
  (v) monoclonal Ig from mouse hybridomas secreting anti-human colorectal carcinoma antibodies
  (VI) monoclonal Ig from mouse hybridomas secreting anti-human melanoma antibodies
  (vii) monoclonal Ig from mouse hybridomas secreting reacting with human leukemia cells
  (viii) monoclonal Ig from mouse hybridomas secreting antibodies reacting with human neuroblastoma cells
  (ix) monoclonal Ig from mouse hybridomas secreting antibodies reacting with human breast cancer antigens
  (x) monoclonal Ig from mouse hybridomas secreting antibodies reacting with human ovarian carcinoma cells
  (xi) monoclonal Ig from mouse hybridomas secreting antibodies reacting with human osteosarcoma cells
  (xii) monoclonal Ig from mouse hybridomas secreting antibodies to lung carcinoma.

As indicated above, the conjugate can also be made with immunoglobulin fragments Ig', referred to also as Fab, Fab' or F(ab')$_2$ or IgM monomer derived from an antibody by, for example, proteolytic enzyme digestion. Such materials and methods of preparation are well known and it may be mentioned that preferred proteolytic enzymes are pepsin and papain. Certain immunoglobulin fragment must be modified prior to conjugation by coupling to one or more peptides, which modification confers an increased resistance of the conjugate made therefrom to continued enzymatic digestion.

Preferred conjugates of the invention are those derived from 4-desacetylvinblastine 3-carboxhydrazide. Preferably the group X in Formula IV takes the value $C_{1-4}$ alkylene and Ig is preferably a monoclonal antibody to a human or animal tumour antigen.

The conjugates of the invention can be prepared by reacting an immunoglobulin or an immunoglobulin fragment with a hemi-acid derivative comprising a vinca moiety having a hydrolyseable bifunctional group attached at the 3-position. More particularly, the process of the invention comprises reacting an immunoglobulin or immunoglobulin fragment with a compound of the formula V-NH-NH-CO-X-CO$Z^1$.

In the above formula, $Z^1$ as defined is sufficiently bulky to inhibit a cyclization reaction while at the same time sufficiently powerful to acylate an amino group on the surface of the immunoglobulin protein. Preferred are those compounds in which $Z^1$ is the residue of an N-acylhydroxylamine, for instance, the N-hydroxysuccinimide esters prepared by use of 1-cyclohexyl-3-(2-morpholinoethyl metho-p-toluenesulphonate or 1,3- dicyclohexyl-carbodiimide. Mixed anhydrides such as those obtained by using isobutyl chloroformate or other bulky $C_{4-7}$ alkylchloroformate are also preferred. When $Z^1$ is an imidazolyl radical, it can be prepared by the use of carbonyl di-imidazole.

Reaction of an immunoglobulin or immunoglobulin fragment with compound of the above formula V-NH-NH-COXCOZ$^1$ is preferably carried out in an aqueous medium and at a temperature of from 5° C. to 25° C., for example at room temperature, and at a pH of 7.5 to 9.5, preferably 8.0. The process results in the attachment by covalent linkage of one or more vinca residues at a free amino or free hydroxy group or free mercapto group of the immunoglobulin molecule, for example, on the amino groups derived from lysine residues. The number of residues attached will depend on the concentration of the reactants and the duration of the reaction but the average number is usually for example from 1 or 3 to 14 or 20, preferably from 2-10.

For example, in carrying out the reaction, a solution of the compound of formula (II) in a suitable solvent such as dimethylformamide is slowly added dropwise to a buffered solution of immunoglobulin in for example 0.34 $\underline{M}$ borate buffer at pH 8.6. The conjugate is isolated by gel filtration and stored in saturated ammonium sulphate solution being readily brought back into solution by dialysis with a buffer solution for example a phosphate buffered saline pH 7.4, or alternatively it can be stored in a refrigerator at 4° C. or frozen at for example $-20°$ C.

Evaluation of the conjugate can be carried out using well known techniques such as affinity chromatography. The efficacy of the conjugate can be estimated by counting the number of viable cells after treatment of a suspension of tumour cells with the conjugate, or from measurements of the uptake of tritiated uridine. Protein and drug concentrations are determined by measuring optical densities of conjugate solutions at two wavelengths, for example 270 and 280 nm, and relating the values obtained to those for the free drug and unconjugated immunoglobulin at the same two wavelengths.

The novel conjugates of the invention are useful in the treatment of cancers and as such are preferably prepared for use in formulations suitable for injection. Thus the invention includes a pharmaceutical formulation, for example an injectable preparation, comprising a conjugate of the invention together with a pharmaceutically-acceptable carrier or diluent such as are well known in the art. It is preferably in unit dosage form each dosage containing for example from 0.01 to 10 mg of the active ingredient (in terms of the vinca drug moiety).

The novel conjugates are effective over a wide dosage range and for example for the treatment of adult humans suffering from cancer dosages per week will normally fall within the range of 1 to 10 mg/kg (vinca drug moiety), more usually in the range of from 3 to 9 mg/kg. However it will be understood that the amount of compound actually administered will be determined by a physician in the light of the relevant circumstances, including the condition to be treated and the chosen route of administration.

We claim:

1. A compound of the formula:

V-NH-NH-CO-X-CO-Z wherein V is a dimeric indole-dihydroindole alkaloid radical of the formula

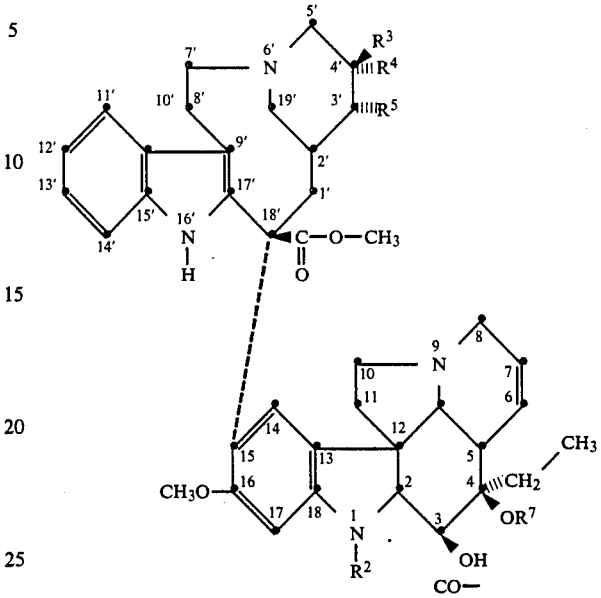

wherein $R^2$ is H, $CH_3$ or CHO; when $R^4$ and $R^5$ are taken singly, $R^5$ is H, and one of $R^3$ and $R^4$ is ethyl and the other is H or OH; or when $R^4$ and $R^5$ are taken together with the carbons to which they are attached, they form an oxirane ring in which case $R^3$ is ethyl; and $R^7$ is H, $C_{1-3}$ alkyl-CO or chloro substituted $C_{1-3}$ alkyl-CO; X is $C_{1-4}$ straight chain alkylene, $C_{2-8}$ branched chain alkylene, $C_{2-4}$ alkenylene, $C_{2-4}$ alkynylene, $C_{3-6}$ cycloalkylene, phenylene, or a direct bond; Z is $NH_2$, NH-$NH_2$, OH, O-$C_{1-3}$ alkyl, succinimidoxy, phthalimidoxy, benzotriazolyloxy, O-CO-$C_{4-7}$ alkyl, $CCl_3CH_2O$, $CBr_3CH_2O$, $CH_2ICH_2O$, benzyloxy, methylbenzyloxy, t-butyloxy, allyloxy, methoxybenzyloxy, nitrobenzyloxy, phenacyloxy, nitrophenacyloxy, methoxyphenacyloxy, methylphen-acyloxy, diphenylmethyloxy, trityloxy(triphenylmethyloxy) or trimethylsilyoxy and acid addition salts thereof.

2. A compound according to claim 1 in which Z is OH, $NH_2$, $NHNH_2$ or $C_{1-3}$ alkyl.

3. A compound according to claim 2 in which Z is methoxy.

4. A compound according to claim 2 in which Z is OH.

5. A compound according to claim 1 in which $Z^1$ is succinimidoxy, phthalimidoxy, benzotriazolyloxy, or $C_{4-7}$ alkyl—CO—O.

6. A compound according to claim 1 in which $Z^2$ is $CCl_3CH_2$-O, $CBr_3CH_2O$, $CH_2ICH_2O$, benzyloxy, methylbenzyloxy, t-butyloxy, allylmethoxybenzyloxy, phenacyloxy, nitrophenacyloxy, methoxyphenacyloxy, methylphenacyloxy, diphenylmethyloxy, trityloxy, or trimethylsilyloxy.

7. A compound according to claim 1 in which X is $C_{1-4}$ straight chain alkylene.

8. A compound according to claim 1 in which X is $C_{2-4}$ alkenylene.

9. A compound according to claim 7 in which X is $CH_2$—$CH_2$.

10. A compound according to claim 1, said compound being $N^2$-succinoyl 4-desacetyl VLB 3-carboxhydrazide.

11. A compound according to claim 1, said compound being $N^2$-succinoyl 4-desacetyl VLB 3-carboxhydrazide, methyl ester.

12. A compound according to claim 1 said compound being $N^2$-adipoyl 4-desacetyl VLB 3-carboxhydrazide methyl ester.

13. A compound according to claim 1, said compound being $N^2$-glutaroyl 4-desacetyl VLB 3-carboxhydrazide.

* * * * *